United States Patent [19]
Chen

[11] Patent Number: 5,154,611
[45] Date of Patent: Oct. 13, 1992

[54] ENDODONTIC INSTRUMENT

[76] Inventor: Calvin C. Chen, 6738 W. Kerry La., Glendale, Ariz. 85308

[21] Appl. No.: 594,281

[22] Filed: Oct. 9, 1990

[51] Int. Cl.$^5$ ............................................. A61G 15/00
[52] U.S. Cl. ................................... 433/77; 433/72; 433/102; 206/369; 206/63.5
[58] Field of Search .................. 433/72, 104, 165, 81, 433/77, 141; 408/241 S, 202; 206/63.5, 369, 375

[56] References Cited

U.S. PATENT DOCUMENTS

| | | | |
|---|---|---|---|
| 3,330,040 | 7/1967 | Kahn | 433/72 |
| 3,358,826 | 12/1967 | Siegel | 206/368 |
| 3,781,996 | 1/1974 | Saffro | 433/75 |
| 4,382,788 | 5/1983 | Pelerin | 433/102 |
| 4,734,035 | 3/1988 | Cheng et al. | 433/102 |
| 4,828,113 | 5/1989 | Friedland et al. | 206/63.5 |

FOREIGN PATENT DOCUMENTS

| | | | |
|---|---|---|---|
| 0171830 | 2/1986 | European Pat. Off. | 408/202 |
| 0205937 | 12/1986 | European Pat. Off. | 433/102 |
| 1271500 | 11/1986 | U.S.S.R. | 433/102 |

Primary Examiner—Cary E. O'Connor

[57] ABSTRACT

An endodontic device for instrumenting a root canal includes an elongated wire, a handle at one end of the wire, and one or more movable stops extending a portion of the wire and abutting on the handle. The length of the portion of the wire which protrudes from the stop(s) constitutes the working length for the root canal treatment. The working length is maintained the same during the treatment, since the stopping means is sandwiched by two stiff objects, namely, the tooth being treated and the rigid object. Also disclosed are (1) a set of movable stops of specific thicknesses for precisely setting a range of working lengths, and (2) a container for storing the set.

8 Claims, 2 Drawing Sheets

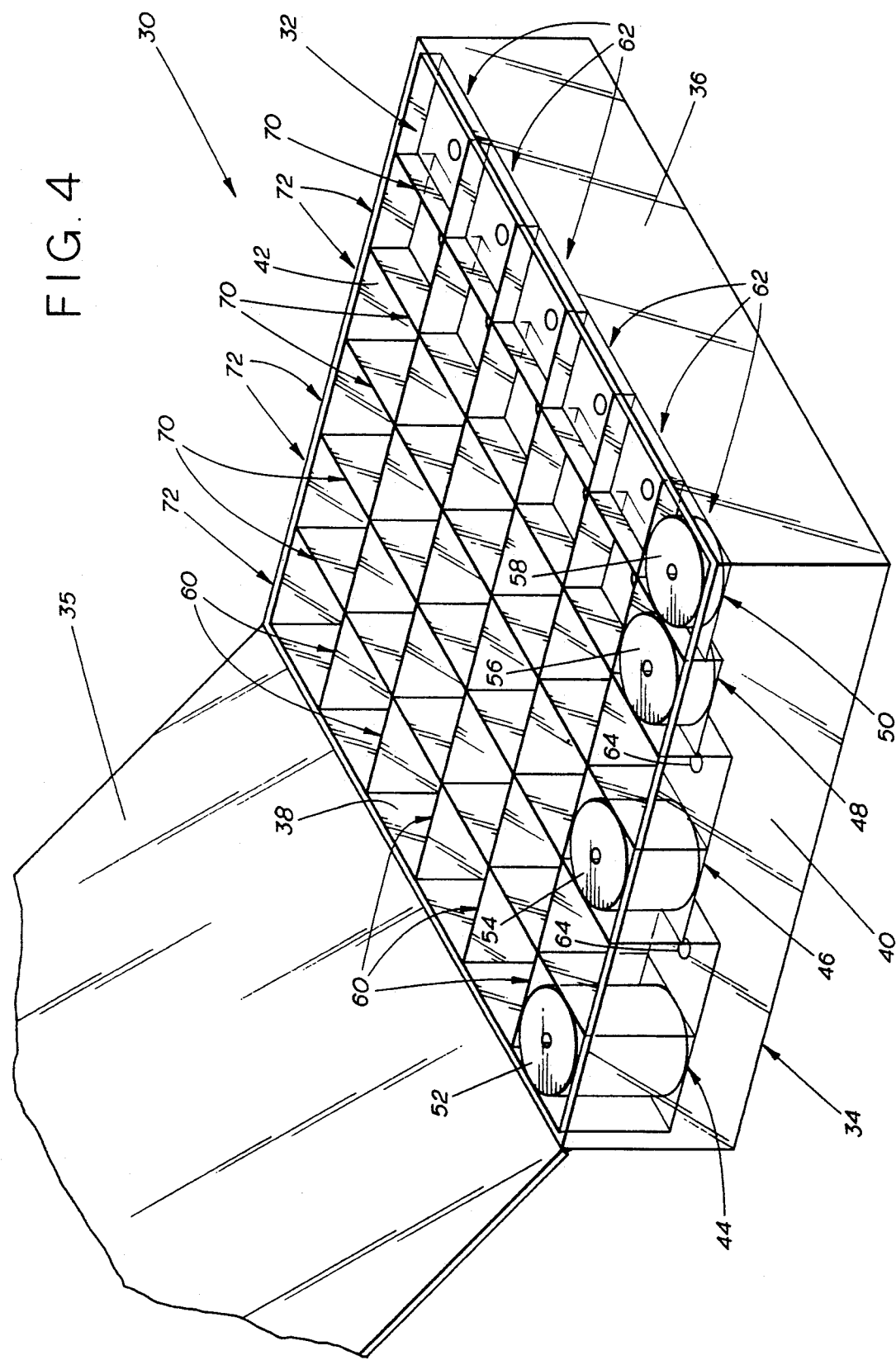

ENDODONTIC INSTRUMENT

FIELD OF THE INVENTION

This invention relates generally to endodontic instruments used in root canal treatment, and particularly to those used for the penetration, boring, drilling, widening and remodeling of root canals before obturation thereof.

BACKGROUND OF THE INVENTION

In many endodontic operations, it is necessary to successively insert an elongated instrument into, and then pull the same from, the root canal of a tooth in order to thoroughly remove any inflamed or necrotic tissue therein and properly enlarge the canal. The instrumented root canal is subsequently sealed off with aseptic material.

As shown in FIG. 1, the conventional endodontic instrument 10, which is used in the root canal treatment described above, generally consists of a thin, flexible wire 12, with an abrasive surface acting as a file, a reamer, or the like, a handle 16 and a rubber stop 14. The handle 16, which is adapted for gripping by the operator, is securely affixed at one end of the wire 12. The rubber stop 14, on the other hand, is movably attached to the wire 12 and can be easily relocated therealong.

The position of the stop 1 at the wire 12 determines the working length 18 of the instrument 10, i.e., the length of the wire 12 to be embedded in the tooth during the treatment, since the stop 14 prevents further penetration of the wire 12 into the canal in the tooth when its bottom surface bumps onto the incisal edge or cusp tip of the tooth being treated.

There are several drawbacks associated with the conventional instrument. For example, the stop 14 may slip without being noticed by the operator during the treatment, thereby causing over-instrumentation or under-instrumentation of the canal.

Also, while the working length 18 is usually determined by radiography, adjustment of the position of the stop 14 by relocating it along the wire 12 is usually required. Thus, the stop 14 may be incorrectly positioned by the operator because of his or her biases or inexperience.

Similarly, when preparing a series of endodontic instruments of various diameters to be used in treating the same canal, there may be discrepancies of the working lengths among the instruments because of the operator's biases or inexperience. This greatly increases the possibility of incomplete instrumentation or even perforation of the canal.

SUMMARY OF THE INVENTION

Accordingly, it is a general object of the present invention to provide an endodontic instrument whose working length, once set, remains the same throughout the root canal treatment.

It is another object of the present invention to provide an endodontic instrument adjustment of whose working lengths minimizes biases or inexperience of the operator.

It is still another object of the present invention to provide an endodontic instrument whose working length can be easily set so that it is identical to that of another instrument without resorting to the subjective judgment of the operator.

Other objects will, in part, be obvious and will, in part, appear below.

The invention accordingly comprises the features of construction, combination of elements and arrangement of parts which will be exemplified in the following detailed description, and the scope of the invention will be indicated in the claims.

Briefly and generally, one embodiment of the present invention is an endodontic instrument comprising three parts: an elongated wire, a rigid object securely affixed at a predetermined point on the wire, and a stopping means which extends along a portion of the wire and abuts on the rigid object. The length of the portion of the wire which protrudes from the stopping means constitutes the working length. In other words, the working length equals the difference between the length of the stopping means and the length of the wire beyond the rigid object. The working length for this instrument is maintained the same during the root canal treatment, since the stopping means is sandwiched by two stiff objects, namely, the tooth being treated and the rigid object.

Another embodiment of the present invention comprises a set of stop units of different thicknesses. The stop units in the set are dimensioned so that specific combinations of the thicknesses of the units result in a number of desired lengths for stopping means. Further, the stop units can be movably attached to the wire. Therefore, attachment of the stop unit(s) in different combinations to the wire constitutes a stop means of a desired length, and thus enables one to attain a specific working length for the instrument.

Still another embodiment of the present invention comprises a container for storing the above-described stop units. In this container, disposed between its top and bottom faces is at least one panel on which, preferably, at least one hole is formed. With such construction, a stop unit properly seated on the hole can be easily picked up by penetrating the wire of an instrument through it and the hole.

BRIEF DESCRIPTION OF THE DRAWINGS

The above and further advantages of the invention may be better understood by referring to the following description in conjunction with the accompanying drawings, in which:

FIG. 4 is a perspective view of a container in accordance with another embodiment of the present invention.

Figure 3:
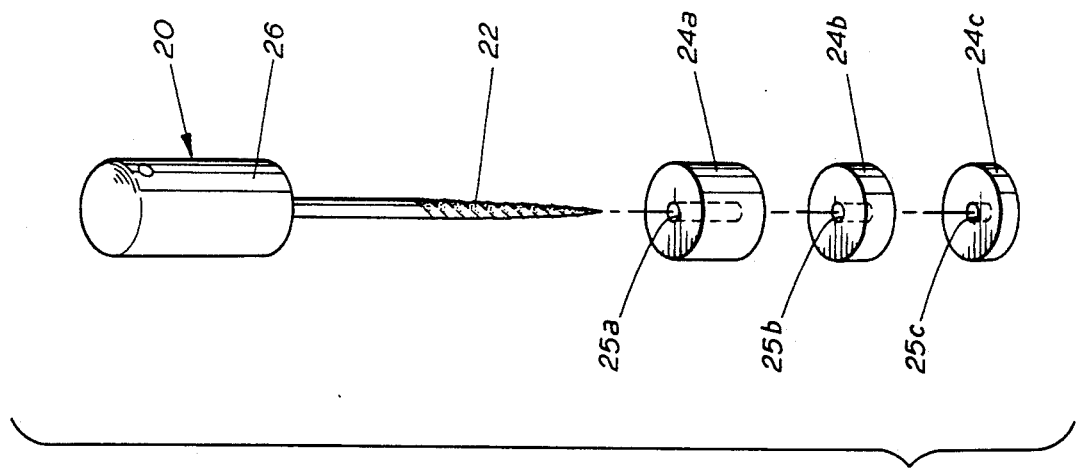
FIG. 3 is an exploded view of the FIG. 2 invention.

In all the drawings, identical numerals represent respectively identical elements. Various elements shown in the drawing are not necessarily in proportion to their actual sizes. Further, as used herein, the terms such as "upward", "downward", "underside", "upper surface" and the like are intended only to denote relative direction solely with reference to the illustrations in the accompanying drawings.

DETAILED DESCRIPTION OF ILLUSTRATIVE EMBODIMENTS

Figure 2:
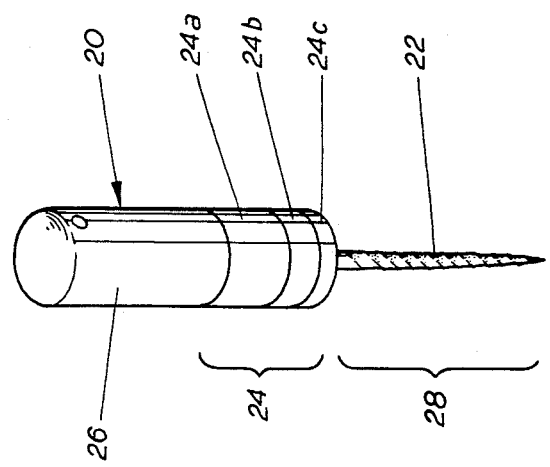
FIG. 2 is a perspective view of an endodontic instrument in accordance with one embodiment of the present instrument.

An endodontic instrument embodying the present invention is generally designated by numeral 20 as shown in FIG. 2. The instrument 20 comprises an elongated wire 22, stopping means 24, and a handle 26. The stopping means 24 further comprises three rubber stop units 24a, 24b and 24c.

As more clearly shown in FIG. 3, the handle 26, which is made of rigid material, is securely attached to the wire 22 by any proper means. The rubber stop units 24a, 24b and 24c, on the other hand, are resilient discs with relatively flat upper and lower surfaces. The rubber stop units 24a, 24b and 24c are movably attached to the wire 22 by penetrating the wire 22 through the centers of their upper and lower surfaces. Once penetration by the wire 22 of all three stop units 24a, 24b and 24c is complete, they are pushed upward along the wire 22 until they abut on each other and also, as a whole, abut on the handle 26. Note that the stop unit 24a, 24b or 24c may be pre-perforated to form a centrally disposed passage 25a, 25b or 25c extending through its entire thickness, if desired. Provision of such passages 25a, 25b and 25c facilitates penetration by the wire 22 through the stop units 24a, 24b and 24c.

Referring back to FIG. 2, in an assembled instrument 20, the stop units 24a, 24b and 24c are held in place by frictionally gripping the wire 22. The portion of the wire 22 that is not embedded in the rubber stop units 24a, 24b and 24c constitutes the working length 28 of the instrument 20.

It is preferable that all the parts in the instrument shown in FIG. 2 be autoclavable, so that they can be conveniently sterilized before use. It is also preferable that the stop units 24a, 24b and 24c be made of radio-opaque material. This will enable one to determine the precise working length for a specific canal by irradiating the canal into which the wire 22 of the FIG. 2 instrument 20 is inserted with X-ray using the technique well known in the art.

Since the upward movement of the rubber stop units 24a, 24b and 24c is constrained by the handle 26 when the instrument 20 is being used to treat a canal, the working length 28 will never become longer because of accidental slip. Moreover, the working length 28 can always be maintained at a predetermined value during the root canal treatment even though unintended downward movement of the stop units 24a, 24b and 24c, which shortens the protruding portion of the wire 22, may occur. This is because, during the treatment, the underside of the lowest stop unit, i.e., 24c in the FIG. 2 instrument, is routinely pushed against a reference point on the surface of the tooth being treated to ensure a thorough insertion into the canal. In other words, any accidental downward movement of the stop units 24a, 24b and 24c is corrected upon each insertion of the wire 22 into the canal, and the preset working length 28 is thus maintained throughout the endodontic operation.

Figure 1:
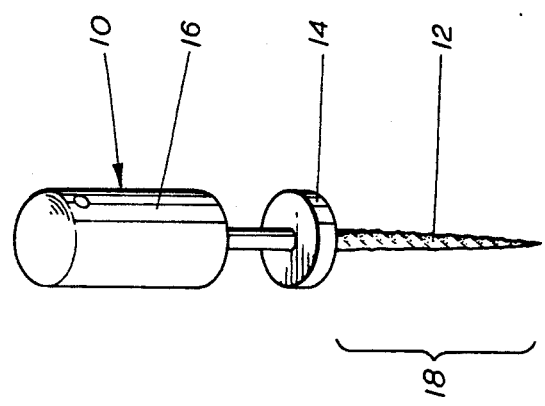
FIG. 1 is a perspective view of a conventional endodontic instrument.

Note that one of the most important features of the FIG. 2 embodiment is the lack of any space between the upper surface of the stop means 24 (i.e., the upper surface of the stop unit 24a) and the handle 26. This feature prevents any upward movement of the stopping means 24. By contrast, in the prior art instrument, which is shown in FIG. 1, there is always a free wire that extends between the handle 16 and the stop 14. In this light, while three stop units 24a, 24b and 24c of different thicknesses are attached to the wire 22 in the FIG. 2 embodiment, an instrument with only one stop unit, for example, that is attached to the wire and pressed against the handle is also within the scope of the invention.

As shown in FIG. 2, the combined thickness of the stop units 24a, 24b and 24c constitutes the length of the stopping means 24, which in turn determines the length of the free portion of the wire, or the working length 28, of the instrument 20. Thus, the working length 28 of the instrument 20 can be easily set by attaching a predetermined number of stop units with predetermined thicknesses to the wire 22.

Another embodiment of the present invention comprises a set of six stop units with four different thicknesses, i.e., two 3 mm-thick units, two 2 mm-thick units, one 1 mm-thick unit and one 0.5 mm-thick unit. Table I illustrates that by attaching one or more rubber stop units selected from this six-unit set to a 21 mm-long wire in the manner described above, one is able to set at least fourteen different working lengths ranging from 14 mm to 20.5 mm in steps of 0.5 mm.

Note that at most three stop units have to be attached to the wire in employing this embodiment to set different working lengths. Also, two identical stop units, namely, those of 3 mm and 2 mm thicknesses, are used in some combinations, e.g., see Table I, rows 1 and 6 under the heading "Combination". Thus, it is necessary to supply two stop units of these thicknesses in this set. Preferably, each of the four thicknesses is designated with a different color or shape so that the unit stop of a specific thickness can be readily identified by the operator. It is also preferable that the stop units be pre-perforated to facilitate penetration by the wire.

TABLE I

| Combination[1] | Length of Stopping Means[2] | Working Length[3] |
|---|---|---|
| 2A + C | 7.0 mm | 14.0 mm |
| 2A + D | 6.5 mm | 14.5 mm |
| 2A | 6.0 mm | 15.0 mm |
| A + B + D | 5.5 mm | 15.5 mm |
| A + B | 5.0 mm | 16.0 mm |
| 2B + D | 4.5 mm | 16.5 mm |
| 2B | 4.0 mm | 17.0 mm |
| B + C + D | 3.5 mm | 17.5 mm |
| B + C | 3.0 mm | 18.0 mm |
| B + D | 2.5 mm | 18.5 mm |
| B | 2.0 mm | 19.0 mm |
| C + D | 1.5 mm | 19.5 mm |
| C | 1.0 mm | 20.0 mm |
| D | 0.5 mm | 20.5 mm |

[1] A, B, C and D represent rubber stops with thicknesses of 3 mm, 2 mm, 1 mm and 0.5 mm, respectively
[2] The length of stopping means is the sum of the thickness(es) of the stop(s) attached to the wire which is 21 mm in length.
[3] The working length is the difference between the length of the wire, i.e., 21 mm, and the length of the stopping means.

The set of stop units described above is an illustrative, non-limiting example which serves the sole purpose of demonstrating how one can assemble, from an assortment of stop units, an endodontic instrument, similar to that shown in FIG. 2, with a predetermined working length. Thus, a person skilled in the art, based on this example, will be able to provide various sets of stop units with thicknesses different from part or all of those set forth above, so that attachment of the stop unit(s) from each set to the wire of an endodontic instrument enables one to attain a desired range of working lengths. In this context, it is to be noted that the stops provided by the suppliers as a part of the prior art instrument, as shown in FIG. 1, are of one uniform thickness and only one stop is attached to the wire of the instrument at all times.

As discussed above, one advantage of the endodontic instrument embodiment of the present invention is that the working length, once set, is maintained at the same value throughout the root canal treatment. The instrument is also advantaged in that, with a set of stop units such as those shown in Table I, an accurate working length can always be attained by attaching to the wire a predetermined number of stop units, each of which is of a specific thickness. Thus, precisely identical working lengths can be set for a number of endodontic instruments. Note that a series of endodontic instruments with wires of different diameters or shapes, yet of identical working lengths, are usually required to treat the same canal.

In contrast, adjustment of the position of a rubber stop along the wire of a conventional instrument (see FIG. 1) requires visual measurements of lengths with the aid of a scale. Thus, the precision of the position adjusted is in large part determined by the operator's vision. As a result, reproduction of precisely identical working lengths for a series of endodontic instruments is a rather difficult, if not impossible, task.

FIG. 4 depicts a container, designated at numeral 30, for storing six sets of the stop units described in Table I and its accompanying text. The container 30, which is rectangular in appearance, comprises one open top face 32, one bottom wall 34 and four side walls 36, 38, 40 and 42. Preferably, the container 30 is made of transparent or translucent material so that its contents can be clearly seen from the outside without removing its cover 35 to expose the top face 32. The cover 35 for the FIG. 4 container 30 is of flap type. However, a slide-type cover can also be adopted, if desired. It is also preferable that the container 30 be made of material which is resistant to relatively high temperatures and pressures so that it can be conveniently sterilized in a conventional autoclave.

Four panels 44, 46, 48 and 50, which parallel the top face 32 and the bottom wall 34, are provided in the container 30 to seat the stop units 52, 54, 56 and 58 of different thicknesses. In particular, the panel 44 is about 3 mm away from the top face 32 so that an upright 3 mm-thick stop unit 52 can rest thereon without protruding above the open face 32 of the container 30. Similarly, the panels 46, 48 and 50 are so disposed as to be able to receive in a like manner the 2 mm unit 54, 1 mm unit 56 and 0.5 mm unit 58, respectively. Note that the stop units shown in FIG. 4 are pre-perforated to facilitate their removal from the container 30 in a manner to be described below.

The lengths of panels 44, 46, 48 and 50 are coextensive with one dimension of the container 30. Two sets of parallel panels 60 and 70 are further provided to divide the container 30 into six rows 62 and six columns 72, respectively. Each row 62 contains six compartments and is capable of accommodating six stop units of the above-described set, namely, two 3 mm and 2 mm units and one 1 mm and 0.5 mm unit, with one unit in one compartment. Note that each compartment is so dimensioned as to snugly accommodate one stop unit of a specific thickness.

Since each of the rows 62 can accommodate one six-unit set, a total of six identical sets can be stored in the container 30. It is preferable that a container for storing stop units be capable of accommodating a plurality of identical sets of stop units. As mentioned above, a series of endodontic instruments of different diameters, which are set to attain an identical working length, are usually required to treat one root canal. Thus, it is convenient to provide such a container so that a series of instruments with an identical working length can be prepared from the stop units stored therein without resorting to stop units stored in another container.

Snug confinement of each stop unit in its compartment is preferred, since it keeps the stop units in their upright position even when the container 30 is being moved from one place to another, e.g., from an autoclave to a storage cabinet. Also, as will become more clearly below, such snug confinement greatly facilitates retrieval of the stop units from the container 30.

The width of panels 44 and 46 is two times that of panels 48 and 50 so that the former can accommodate two stop units 52 or 54 in a row 62 (only one is shown) while the latter can accommodate only one unit 56 or 58. This feature is necessitated, since the set of stop units to be stored in the container 30 consists of two 3 mm units, two 2 mm units, one 1 mm unit and one 0.5 mm unit.

Preferably, a hole 64 is formed about the center of the bottom wall of each compartment. Further, the height of the container 30 is preferably greater than 5 mm, so that all the holes 64 are at least 2 mm away from the bottom wall 34 of the container 30.

To set a specific working length of an instrument, one first consults a chart similar to Table I to determine which combination of stop units to be used. Then, the wire of the instrument is directed to penetrate one of the stop units in that combination while the stop unit to be penetrated remains in the container 30 during the entire penetration process. Once that stop unit has been penetrated through its entire thickness by the wire, it is frictionally engaged with the wire and thus can be easily picked up from the container 30. A second or third stop unit can be retrieved by the same wire from the container 30 in a similar manner, if necessary.

Pre-perforation of stop units enables one to aim and penetrate the unit without much difficulty. So does snug confinement of each stop unit in its compartment, since the unit remains rather steady in its upright position during the entire retrieval process as described above. Note that coplanarity of the upper surfaces of the stop units with the top face of the container, as shown in FIG. 4, also promotes accurate aiming, since the stop units are presented as nearly to the eye of the operator as possible while not protruding above the top face.

The stop unit is so positioned in its compartment such that the wire, once penetrating the passage, enters the hole 64 formed on panel 44, 46, 48 or 50. Provision of holes 64 and some space between the holes 64 and the bottom wall 34 serves to prevent the wire from bumping into a hard surface and becoming bent when the penetration is complete. Further, when the container 30 is made of transparent or translucent material, one can also avoid the just-mentioned bending problem by cautiously watching the penetration of the wire.

The foregoing description has been limited to specific embodiments of this invention. It will be apparent, however, that variations and modifications may be made to the invention, with the attainment of some or all of the advantages of the invention.

For example, while a handle is used as the upper limit against movement of the stopping means in the instrument embodiment shown in FIG. 2, any rigid object securely attached at one proper point on the wire can also perform this function.

Also, in the container embodiment shown in FIG. 4, three sets of panels intersect to form a plurality of compartments, each of which snugly receives a stop unit. Confinement of stop units to limit their movement can also be achieved by forming recessive sockets on the horizontal panels and seating the stop units in the sockets.

Therefore, it is the object of the appended claims to cover all such variations and modifications as come within the true spirit and scope of the invention.

What is claimed is:

1. A box-like container for storing a set of stop units for an endodontic instrument, which container comprises:

an open top face and a bottom wall which are spaced from each other by a distance greater than the thicknesses of any of the stop units;

at least one panel disposed between the top face and the bottom wall so that the stop units are capable of uprightly resting thereon, at least one hole being formed on the panel where the stop units are to be uprightly seated; and means for limiting movement of the stop units uprightly resting on the panel.

2. The container as defined in claim 1, wherein the panel is spaced from the top face so that the stop units uprightly resting thereon do not protrude above the top face.

3. The container as defined in claim 1, wherein the panel is spaced from the top face so that the upper surfaces of the stop units uprightly resting thereon are generally coplanar with the top face.

4. The container as defined in claim 1, wherein the limiting means includes partitions so constructed as to closely surround the stop units uprightly resting on the panel.

5. The container as defined in claim 1, wherein the container is made of autoclavable material.

6. The container defined in claim 1, wherein the container is made of diaphanous material.

7. The container as defined in claim 1, further comprising a cover for the top face.

8. The container as defined in claim 7, wherein the cover is of flap type.

* * * * *